United States Patent

Fory et al.

[11] 4,225,336
[45] Sep. 30, 1980

[54] PHENOXYALKYLOXAZOLINES, AS SELECTIVE HERBICIDES IN CEREALS

[75] Inventors: Werner Föry, Basel; Hermann Rempfler, Ettingen, both of Switzerland; Georg Pissiotas, Lörrach, Fed. Rep. of Germany; Otto Rohr, Therwil; Beat Böhner, Binningen, both of Switzerland

[73] Assignee: Ciba-Geigy Corporation, Ardsley, N.Y.

[21] Appl. No.: 62,191

[22] Filed: Jul. 30, 1979

Related U.S. Application Data

[63] Continuation-in-part of Ser. No. 974,195, Dec. 28, 1978, abandoned.

[30] Foreign Application Priority Data

Jan. 2, 1978 [CH] Switzerland ................................. 2/78

[51] Int. Cl.$^2$ ............................................. A01N 9/28
[52] U.S. Cl. ............................................. 71/88; 71/94; 546/275; 548/237; 548/238
[58] Field of Search ................................. 71/88, 94

[56] References Cited

U.S. PATENT DOCUMENTS

| | | | |
|---|---|---|---|
| 3,877,921 | 4/1975 | Timmons et al. | 71/88 |
| 4,046,553 | 9/1977 | Takahashi et al. | 71/94 |
| 4,133,675 | 1/1979 | Schurter et al. | 71/94 |

Primary Examiner—Paul M. Coughlan, Jr.
Attorney, Agent, or Firm—Frederick H. Rabin

[57] ABSTRACT

Phenoxyalkyloxyzolines corresponding to the formula

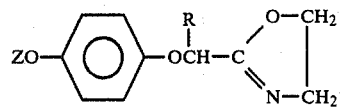

wherein
  R is hydrogen or methyl
  Z is a Phenyl-or Pyridyl-radical

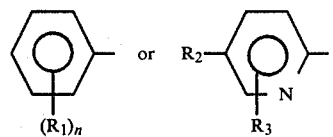

$R_1$ is halogen, trifluoromethyl, cyano or nitro
$R_2$ is hydrogen, halogen or cyano
$R_3$ is halogen trifluoromethyl or cyano and
n is 1 or 2.

are effective herbicides which are tolerant towards cereal.

4 Claims, No Drawings

PHENOXYALKYLOXAZOLINES, AS SELECTIVE HERBICIDES IN CEREALS

CROSS-REFERENCE TO RELATED APPLICATION

This is a continuation-in-part of our application Ser. No. 974,195, filed Dec. 28, 1978, now abandoned.

DETAILED DISCLOSURE

The present invention relates to herbicidal nuclear substituted phenoxyalkyloxazolines, herbicidal compositions which contain these compounds as active ingredients, and to methods of selectively controlling weeds in crops of cereals.

The active compounds (active substances) of the present invention have the formula I

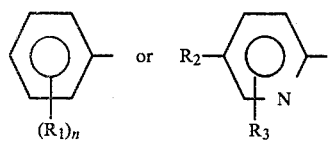

wherein
R represents hydrogen or methyl and
Z represents a substituted phenyl radical or pyrid-2-yl radical

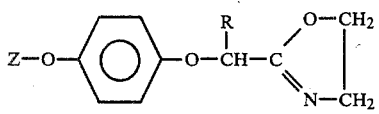

wherein
$R_1$ represents halogen, trifluoromethyl, cyano or nitro,
$R_2$ represents hydrogen, halogen or cyano,
$R_3$ represents halogen, trifluoromethyl or cyano, and
n is 1 or 2.

By halogen is meant each halogen atom, preferably chlorine or bromine.

That phenoxyalkyloxazolines can be used as herbicides and growth regulators is known from U.S. Pat. No. 3,877,821. Herbicidal compositions which contain similar phenoxyphenoxyalkyl heterocyclic compounds as active ingredients are described in German Offenlegungsschrift 2,613,697. Three of these oxazolines are disclosed in the published Japanese Patent Publication No. 52 139 034.

The present phenoxyalkyloxazolidines exhibit an effective herbicidal action when employed in low rates of application and surprisingly do not harm cerals in spite of their good action against monocotyledonous weeds.

The phenoxyalkyloxazolines of the present invention have a low toxicity to warm-blooded animals and their application is unlikely to cause problems. The proposed rates of application are between 0.1 and 5 kg per hectare.

The compounds of the formula I are obtained by known reaction methods of chemical synthesis.

In a first process, phenoxyalkylethyleneimides of the formula II

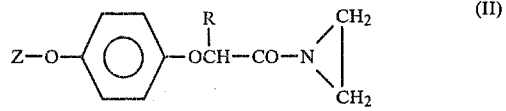

wherein R and Z are as defined for formula I, are obtained by rearrangement of the aziridinyl amide under the influence of the iodide ion, in a solvent.

Instead of the ethyleneimide, it is also possible to subject a phenoxyalkylethylamide of the formula III

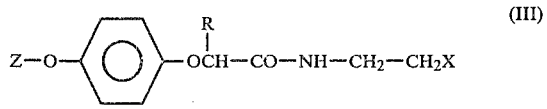

wherein R and Z are as defined for formula I, whilst X can be the OH group, a halogen atom or a sulfonic acid radical, to cyclisation in a solvent.

Suitable solvents are in particular aprotic water-soluble solvents, such as low molecular alcohols, ketones, dimethyl formamide, dimethyl sulfoxide, and also chlorinated hydrocarbons.

The cyclisation is carried out in the presence of a base, for example an alkali metal hydroxide or a quaternary ammonium hydroxide if X represents a halogen atom or a sulfonic acid radical, but under acid conditions, for example in the presence of sulfuric acid, if X represents the hydroxyl group.

Suitable catalysts for the cyclisation are the alkali metal salts or tertiary ammonium salts of halides and sulfonic acids.

The cyclisation occurs at room temperature, but the reaction mixture can be heated to the boil in order to hasten the procedure.

A further route for obtaining the phenoxyalkyloxazolines of the formula I consists in condensing a para-phenoxyphenol or para-pyrid-2-yloxyphenol of the formula IV

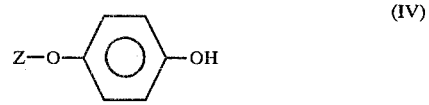

wherein Z represents a phenyl or pyridyl radical defined under formula I, with a 2-oxazoline-alkyl halide of the formula V

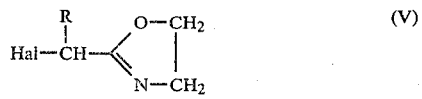

wherein Hal represents a halogen atom and R is as defined for formula I, in the presence of an acid acceptor.

This reaction is also carried out in a water-miscible solvent or else in a halogenated hydrocarbon, under normal pressure and at a temperature which can be between room temperature and the boiling point of the reaction mixture. Preferably, the reaction mixture is refluxed.

The acid acceptor can be an aqueous alkali metal hydroxide, such as KOH and NaOH, and also another base, such as ammonia, a carbonate ($K_2CO_3$, $NaHCO_3$), an alcoholate ($NaOCH_3$, potassium tert-butylate), and also an organic base, such as triethylamine etc. If an organic base is already employed as solvent, for example pyridine, then it acts simultaneously as acid acceptor.

The starting materials of the formula II are most desirably obtained by amidation from the corresponding phenoxyphenoxypropionic acids and pyridyloxyphenoxypropionic acids, for example those described in German Offenlegungsschrift 2,223,894, 2,531,643, 2,546,251 and 2,652,384.

The amidation is carried out by methods which are in themselves known by reacting the halides or the anhydride of these acids with ethyleneimine, the corresponding haloethylamines, or with a 2-amino-ethyl sulfonate.

The following Examples illustrate a process of the present invention for obtaining such compounds. Parts and percentages are by weight. Further compounds obtained in analogous manner are listed in the subsequent table.

EXAMPLE 1

2-{1-[4'-(3'',5''-Dichloropyrid-2''-yloxy)-phenoxy]ethyl}oxazoline 50 g of 50% NaOH and 1 g of tetrabutylammonium bromide are added to 39 g (0.1 mole) of α-[4-(3',5'-dichloropyrid-2'-yl)-oxy-phenoxy]propionic acid chloroethylamide in 500 ml of methylene chloride. After stirring for 4 hours at room temperature, 50 ml of water are added and the methylene chloride phase is separated, dried over magnesium sulfate and concentrated. A small amount of ether is added to the oily residue, whereupon the product crystallises. The crystals are collected by filtration and dried, affording 25.3 g of final product with a melting point of 111°-113° C. (known)

EXAMPLE 2

2-{1-[4'-(4''-Trifluoromethylphenoxy)-phenoxy]ethyl}-oxazoline

A suspension of 25.4 g of 4-(4'-trifluoromethylphenoxy)-phenol, 23.6 g of α-bromopropionic acid-2-chloroethylamide and 20 g of anhydrous potassium carbonate in 250 ml of ethylene methyl ketone is stirred for 18 hours at reflux temperature. The reaction mixture is filtered and the filtrate is concentrated in vacuo. The oily residue (19.5 g) is dissolved in 75 ml of methylene chloride and, after addition of 2.5 g of tetrabutylammonium hydrogen sulfate and of 2.51 g of sodium hydroxide, the solution is stirred for 3 hours at room temperature in a nitrogen atmosphere. The methylene chloride phase is separated, washed with water, dried and concentrated in vacuo, affording 13.6 g of the title compound; $n_D^{20}=1.5274$. (known)

The following compounds are obtained in analogous manner:

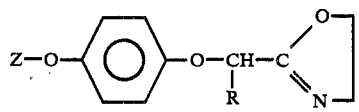

| Compound | Z | R | Physical data |
|---|---|---|---|
| 3 | 2-chloro-4-trifluoromethylphenyl | $CH_3$ | $n_D^{20}$: 1,5391 (known) |
| 4 | 2,4-dichlorophenyl | $CH_3$ | $n_D^{30}$: 1,5764 |

-continued

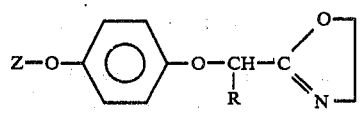

| Compound | Z | R | Physical data |
|---|---|---|---|
| 5 | 3,5-dichloropyridyl-(2) | H | |
| 6 | 4-trifluoromethylphenyl | H | |
| 7 | 4-chloro-2-cyanophenyl | $CH_3$ | $n_D^{23}$: 1,5751 |
| 8 | 4-chlorophenyl | $CH_3$ | $n_D^{23}$: 1,5678 |
| 9 | 4-cyanophenyl | $CH_3$ | $n_D^{23}$: 1,5732 |
| 10 | 4-chloro-2-trifluoromethylphenyl | | |
| 11 | 4-chloro-2-nitrophenyl | $CH_3$ | $n_D^{23}$: 1,5852 |
| 12 | 4-bromo-2-nitrophenyl | $CH_3$ | |

The novel α-[4-(phenoxyphenoxy]- and α-[4-(pyridyloxy)-phenoxy]-alkyloxazolines exhibit a strong herbicidal action in relatively low rates of concentration.

The compounds of the formula I can be used as herbicides in pre-emergent and especially in post-emergent application. Their action is directed in particular against monocotyledonous weeds and they can be used for selective weed control in crops of dicotyledonous plants, for example in soya. However, they are also suitable for selective weed control in crops of certain monocotyledonous plants, for example in cereals, such as wheat and barley.

The present invention also provides herbicidal compositions which contain a compound of the formula I as active component. Such compositions can be in the form of conventional solid formulations (dusts, tracking powders, granules), water-dispersible concentrates (wettable powders, emulsions, emulsifiable concentrates and pastes), or solutions, and are formulated by known methods with corresponding adjuvants and carriers.

The compositions of the present invention are obtained in known manner by homogeneously mixing and grinding active substances of the formula I with suitable carriers, with or without the addition of dispersants or solvents which are inert to the active substances. The active substances can be processed to the following formulations:

solid formulations: dusts, tracking powders, granules (coated granules, impregnated granules and homogeneous granules);

active substance concentrates which are dispersible in water: wettable powders, pastes, emulsions;

liquid formulations: solutions.

The concentration of active substance in the above described compositions is between 0.1 and 95%, preferably between 1% and 80%. Formulations can be diluted to concentrations as low as 0.001%. The rates of application are ordinarily from 0.1 to 10 kg, preferably from 0.25 to 5 kg, of active substance per hectare. The active compounds of the formula I can be formulated for example as follows (parts are by weight):

Dusts

The following substance are used to prepare (a) 5% and (b) 2% dust:

(a)

5 parts of one of the active substances of the formula I 95 parts of talc;

(b)

2 parts of active substance
1 part of highly dispersed silicic acid
97 parts of talc.

The active substances are mixed with the carriers and ground.

Granulate

The following substances are used to prepare a 5% granulate:
- 5 parts of one of the active substances of the formula I;
- 0.25 part of epichlorohydrin;
- 0.25 part of cetyl polyglycol ether;
- 3.25 parts of polyethylene glycol;
- 91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resulting solution is sprayed on kaolin and subsequently evaporated in vacuo.

Wettable Powders

The following constituents are used for prepare (a) a 50%, (b) a 25% and (c) a 10% wettable powder:

(a)

50 parts of one of the active substances of the formula I,
5 parts of sodium dibutylnaphthylsulphonate,
3 parts of naphthalenesulphonic acid/phenolsulphonic acid/formaldehyde condensate (3:2:1),
20 parts of kaolin,
22 parts of Champagne chalk;

(b)

25 parts of the above active substance,
5 parts of sodium oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin;

(c)

10 parts of the above active substance,
3 parts of a mixture of the sodium salts of saturated fatty alcohol sulphates,
5 parts of naphthalenesulphonic acid/formaldehyde condensate,
82 parts of kaolin.

The indicated active substance is applied to the corresponding carriers (kaolin and chalk) and then these are mixed and ground, to yield wettable powders of excellent wettability and suspension power. By diluting these wettable powders with water it is possible to obtain suspensions of the desired concentration of active substance. Such suspensions are used for preemergent control of weeds and grass-like weeds in crops of cultivated plants.

Paste

The following substances are used to manufacture a 45% paste:
- 45 parts of one of the active substances of the formula I,
- 5 parts of sodium aluminium silicate,
- 14 parts of cetyl polyglycol ether with 8 moles of the ethylene oxide,
- 1 part of oleyl polyglycol ether with 5 moles of the ethylene oxide,
- 2 parts of spindle oil,
- 10 parts of polyethylene glycol,
- 23 parts of water.

The active substance is homogeneously mixed with the adjuvants in appropriate devices and ground, yielding a paste from which, by dilution with water, it is possible to obtain suspensions of the desired concentration of active substance. The suspensions are suitable for treating areas of grass.

Emulsifiable Concentrate

The following ingredients are mixed to manufacture a 25% emulsifiable concentrate:
- 25 parts of one of the active substances of the formula I,
- 5 parts of a mixture of nonylphenolpolyoxyethoxyethylene and calcium dodecylenesulphonate,
- 35 parts of 3,5,5-trimethyl-2-cyclohexan-1-one,
- 35 parts of dimethyl formamide.

The active substances of the invention are also of interest for combined application with a number of herbicides of the phenylurea and triazine series in cereal crops, maize, sugar cane and in fruit growing and viticulture.

The following test methods were employed to establish the usefulness of the compounds of the formula I as herbicides (pre- and postemergent control).

Preemergent herbicidal action (germination inhibition)

In a greenhouse, immediately after sowing the test plants in seed dishes the surface of the soil is treated with an aqueous suspension of the active substances obtained from a 25% wettable powder. Four different concentration series were used, corresponding to 4, 2, 1 and 0.5 kg of active substance per hectare respectively. The seed dishes are kept in the greenhouse at 22°–25° C. and 50 to 70% relative humidity. The test is evaluated 3 weeks later according to the following rating:
0=plants undamaged (as untreated control);
1–9=intermediate stages of damage;
10=plants totally withered.

Post-emergent herbicidal action (Contact herbicide)

A large number of weeds and cultivated plants, both mono- and dicotyledonous, were sprayed after emergence in the 4- to 6-leaf stage with an aqueous active substance emulsion in rates to 0.5, 1, 2 and 4 kg of active substance per hectare and kept at 24°–26° C. and 45–60% relative humidity. The test was evaluated, as in the preemergent test, 5 and 15 days after treatment in accordance with the same rating.

Post-emergent action in the field

A field in which winter wheat of the variety "TAM 101" had been sown in October was treated the following spring in March (5 months after sowing) when the wheat had attained the 2–3 leaf stage and avena fatua (wild oats), the most prominent weed, was encountered in the 1–5 leaf stage, in parcels with dilute aqueous active substance emulsions, so that the parcels were sprayed with 2, 1.5, 1, 0.75 and 0.5 kg respectively of active substance per hectare. The test was evaluated after 37 days at the end of April and the state of the wheat and of the wild oats was rated in accordance with the scale referred to above. The results are reported in the following table:

| Compound rate of application in kg/ha | Winter wheat | | | | | avena fatua | | | | |
|---|---|---|---|---|---|---|---|---|---|---|
| | 2 | 1.5 | 1 | 0.75 | 0.5 | 2 | 1.5 | 1 | 0.75 | 0.5 |
| No. 1 | 5 | 3 | 2 | 0 | 0 | 10 | 10 | 9 | 9 | 9 |
| A | 8 | 7 | 7 | 7 | 5 | 10 | 10 | 10 | 10 | 10 |
| Hoe 23 408 | 3 | 2 | 2 | — | 2 | 8 | 8 | 7 | — | 3 |

A = 2-[5-(3',5'-dichloropyridyl-2'-oxy)-phenoxy]-propionic acid methyl ester known from German Offenlegungsschrift 2,546,251 or U.S. Pat. specification 4,046,553
Hoe 23 408 = 2-[4-(2',4'-dichlorophenoxy)-phenoxy]-propionic acid methyl ester known from German Offenlegungsschrift 2,223,894 or U.S. Pat. specification 3,953,442
— This concentration was not tested.

A field in which summer barley of the type "CM-67" had been sown in the middle of February was treated after 42 days at the end of March, when the barley had attained the 4–6 leaf stage, and avena fatua, the most widespread weed, the 5–7 leaf stage, in parcels with dilute aqueous active substance emulsions, so that the parcels were sprayed with 2, 1.5, 1, 0.75 and 5 kg respectively of active substance per hectare. The test was evaluated after 22 days in April and the state of the plants was rated in accordance with the above scale. The results are reported in the following table.

| Plant rate of application in kg/ha | Summer barley | | | | | avena fatua | | | | |
|---|---|---|---|---|---|---|---|---|---|---|
| | 2 | 1.5 | 1 | 0.75 | 0.5 | 2 | 1.5 | 1 | 0.75 | 0.5 |
| Compound No. 1 | 0 | 0 | 0 | 0 | 0 | 10 | 10 | 10 | 10 | 10 |
| A | 9 | 9 | 9 | 7 | 6 | 10 | 10 | 10 | 10 | 10 |
| Hoe 23 408 | 0 | 0 | 0 | — | 0 | 10 | 9 | 6 | — | 5 |

—This concentration was not tested.

We claim:

1. A method for controlling weeds in crops of cereals which comprises applying a herbicidally effective amount of a phenoxyalkyloxazoline of the formula I

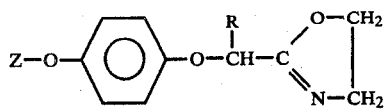

wherein
R represents hydrogen or methyl and
Z represents a substituted phenyl radical or pyrid-2-yl radical

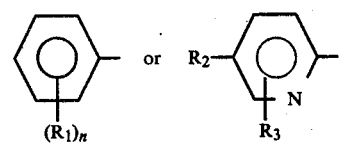

wherein
$R_1$ represents halogen, trifluoromethyl, cyano or nitro,
$R_2$ represents hydrogen, halogen or cyano,
$R_3$ represents halogen, trifluoromethyl or cyano, and
n is 1 or 2;
to an area where cereal crop is growing or expected to grow.

2. A method according to claim 1, wherein the phenoxyalkyloxazoline used is
2-{1-[4'-(3'',5''-dichloropyrid-2''-yloxy)-phenoxy]-ethyl}-oxazoline.

3. A method according to claim 1, wherein the phenoxyalkyloxazoline used is
2-{1-[4'-(4''-trifluoromethylphenoxy)-phenoxy]-ethyl}-oxazoline.

4. The method according to claim 1, wherein the cereal is wheat.